United States Patent
Sjölund et al.

(10) Patent No.: US 11,358,003 B2
(45) Date of Patent: Jun. 14, 2022

(54) GENERATION OF REALIZABLE RADIOTHERAPY PLANS

(71) Applicant: Elekta AB, Stockholm (SE)

(72) Inventors: Jens Olof Sjölund, Stockholm (SE);
Jonas Anders Adler, Stockholm (SE)

(73) Assignee: Elekta AB, Stockholm (SE)

( * ) Notice: Subject to any disclaimer, the term of this patent is extended or adjusted under 35 U.S.C. 154(b) by 610 days.

(21) Appl. No.: 16/352,260

(22) Filed: Mar. 13, 2019

(65) Prior Publication Data
US 2020/0289847 A1  Sep. 17, 2020

(51) Int. Cl.
*A61N 5/10* (2006.01)
*G16H 20/40* (2018.01)
*G06N 20/00* (2019.01)

(52) U.S. Cl.
CPC .......... *A61N 5/103* (2013.01); *A61N 5/1031* (2013.01); *A61N 5/1039* (2013.01); *A61N 5/1081* (2013.01); *G06N 20/00* (2019.01); *G16H 20/40* (2018.01)

(58) Field of Classification Search
CPC .... A61N 5/103; A61N 5/1031; A61N 5/1038; A61N 5/1039; A61N 2005/1041
See application file for complete search history.

(56) References Cited

U.S. PATENT DOCUMENTS

| | | | |
|---|---|---|---|
| 11,077,320 B1* | 8/2021 | Hibbard | G06T 7/0012 |
| 2017/0177812 A1 | 6/2017 | Sjolund | |
| 2018/0043182 A1* | 2/2018 | Wu | G16H 70/20 |
| 2019/0175952 A1* | 6/2019 | Hissoiny | G06N 3/02 |
| 2020/0188692 A1* | 6/2020 | Liu | A61N 5/1031 |
| 2021/0093891 A1* | 4/2021 | Sheng | A61N 5/103 |

OTHER PUBLICATIONS

Amos, Brandon, et al., "Optnet: Differentiable optimization as a layer in neural networks", Proceedings of the 34 th International Conference on Machine Learning, Sydney, Australia, PMLR 70, (2017), 13 pgs.

Sjolund, Jens, et al., "Data-Driven Generation of Realizable Radiotherapy Plans", (Nov. 18, 2018), 8 pgs.

Zarepisheh, Masoud, et al., "A DVH-guided IMRT optimization algorithm for automatic treatment planning and adaptive radiotherapy replanning", Medical physics 41.6, (2014), 14 pgs.

* cited by examiner

*Primary Examiner* — John P Lacyk

(74) *Attorney, Agent, or Firm* — Schwegman Lundberg & Woessner, P.A.

(57) ABSTRACT

Techniques for generating a radiotherapy treatment plan are provided. The techniques include receiving an input parameter related to a patient, the input parameter being of a given type; processing the input parameter with a machine learning technique to estimate a realizable plan parameter of a radiotherapy treatment plan, wherein the machine learning technique is trained to establish a relationship between the given type of input parameter and a set of realizable radiotherapy treatment plan parameters to achieve a target radiotherapy dose distribution; and generating the radiotherapy treatment plan based on the estimated realizable plan parameter.

19 Claims, 6 Drawing Sheets

GENERATION OF REALIZABLE RADIOTHERAPY PLANS

TECHNICAL FIELD

This disclosure relates generally to radiation therapy or radiotherapy. More specifically, this disclosure relates to systems and methods for training and/or predicting data for use in developing a radiation therapy treatment plan to be used during radiotherapy.

BACKGROUND

Radiotherapy is used to treat cancers and other ailments in mammalian (e.g., human and animal) tissue. One such radiotherapy technique is a Gamma Knife, which irradiates a patient with a large number of low-intensity gamma rays that converge with high intensity and high precision at a target (e.g., a tumor). In another embodiment, radiotherapy is provided using a radiotherapy device that accelerates particles (photons, electrons, and/or ions) to irradiate a target in a patient. Another form of radiotherapy is brachytherapy, where a radiation source is placed inside or next to the area requiring treatment. The direction and shape of the radiation beam should be accurately controlled to ensure the tumor receives the prescribed radiation, and the placement of the beam should be such as to minimize damage to the surrounding healthy tissue (often called the organ(s) at risk (OARs)). Treatment planning can be used to control radiation beam parameters, and a radiotherapy device effectuates a treatment by delivering a spatially varying dose distribution to the patient.

Traditionally, for each patient, a radiation therapy treatment plan ("treatment plan") may be created using an optimization technique based on clinical and dosimetric objectives and constraints (e.g., the maximum, minimum, and mean doses to the tumor and critical organs). The treatment planning procedure may include using a three-dimensional (3D) image of the patient to identify a target region (e.g., the tumor) and to identify critical organs near the tumor. Creation of a treatment plan can be a time-consuming process where a planner tries to comply with various treatment objectives or constraints (e.g., dose volume histogram (DVH) objectives), taking into account their individual importance (e.g., weighting) in order to produce a treatment plan which is clinically acceptable. This task can be a time-consuming trial-and-error process that is complicated by the various OARs, because as the number of OARs increases (e.g., 21 are commonly segmented in a head-and-neck treatment), so does the complexity of the process. OARs distant from a tumor may be easily spared from radiation, while OARs close to or overlapping a target tumor may be difficult to spare. Segmentation may be performed to identify the OARs and the area to be treated (for example, a planning target volume (PTV)). After segmentation, a dose plan may be created for the patient indicating the desirable amount of radiation to be received by the PTV (e.g., target) and/or the OARs. The PTV may have an irregular volume and may be unique as to its size, shape, and position. A treatment plan can be calculated after optimizing a large number of plan parameters to ensure that enough dose is provided to the PTV while as low a dose as possible is provided to surrounding healthy tissue. Therefore, a radiation therapy treatment plan may be determined by balancing efficient control of the dose to treat the tumor against sparing any OAR. Typically, the quality of a radiation treatment plan may depend upon the level of experience of the planner. Further complications may be caused by anatomical variations between patients.

Currently, most treatment planning procedures limit the parameters considered to those associated with the specific patient or to the specific treatment session. Experience generated from previously developed treatment plans for the same patient, or similar treatment procedures for patients having the same kind of tumor with similar size and location taking into account potential outcomes (e.g., dose applied, success rate, survival time and the like), however, has not been effectively used in the procedures of developing new plans. What is needed is the ability to utilize previous treatment plans to predict objective parameters for one or more outcomes that may be used to generate a realizable radiation therapy treatment plan, which may provide an optimized dose to be delivered to treat the tumor while minimizing exposure to the one or more OARs.

Overview

In some embodiments, a computer-implemented method, non-transitory computer readable medium, and a system comprising a memory and processor are provided for generating a radiotherapy treatment plan. The method, computer readable medium storing instructions, and processor executes operations including receiving an input parameter related to a patient, the input parameter being of a given type; processing the input parameter with a machine learning technique to estimate a realizable plan parameter of a radiotherapy treatment plan, wherein the machine learning technique is trained to establish a relationship between the given type of input parameter and a set of realizable radiotherapy treatment plan parameters to achieve a target radiotherapy dose distribution; and generating the radiotherapy treatment plan based on the estimated realizable plan parameter.

In some implementations, the input parameter is processed by predicting, using the trained machine learning technique, an estimated treatment plan parameter of the radiotherapy treatment plan based on the input parameter; and generating the realizable plan parameter that corresponds to the estimated plan parameter. In some implementations, the realizable plan parameter is generated by solving an optimization problem.

In some implementations, the optimization problem uses a loss function based on the set of realizable radiotherapy treatment plan parameters and the estimated plan parameter. In some implementations, the optimization problem is solved using at least one of a closed form solution, a gradient based scheme, or a stochastic optimization scheme.

In some implementations, the realizable plan parameter is generated by using at least one of an explicit differentiation process, composition of a fixed number of differentiable iterations, or a differentiable machine learning technique trained to estimate the realizable plan parameter. In some implementations, the estimated treatment plan parameter is incompatible with a radiotherapy device used to treat the patient. In some implementations, the estimated treatment plan parameter corresponds to a first dose distribution that is incompatible with the radiotherapy device, and the realizable plan parameter is generated by identifying a subset of the set of the realizable radiotherapy treatment plan parameters that are compatible with the radiotherapy device and result in a second dose distribution that is within a specified threshold.

In some implementations, the input parameter includes at least one of a medical image, segmentation information of an object of interest associated with the patient, or radiation dose prescription information. In some implementations, the input parameter is further processed to achieve at least one of selected points from a DVH or one or more radiobiological properties. In some implementations, the set of realizable radiotherapy treatment plan parameters includes at least one of machine parameters or a dose distribution.

In some implementations, the machine learning algorithm is trained to establish the relationship between the particular type of input parameter and the set of realizable radiotherapy treatment plan parameters by optimizing a loss function based on a given radiotherapy treatment dose distribution and a given set of realizable radiotherapy treatment plan parameters. In some implementations, the optimization comprises at least one of a closed form solution, a gradient based scheme, or a stochastic optimization scheme.

In some implementations, the machine learning technique is trained by optimizing two loss functions using bilevel optimization. In some implementations, a first of the two loss functions is optimized based on a deviation between the particular type of input parameter and a set of estimated radiotherapy treatment plan parameters; and a second of the two loss functions is optimized based on a deviation between a result of optimizing the first loss function and realizable radiotherapy treatment plan parameters corresponding to the set of estimated radiotherapy treatment plan parameters.

The above overview is intended to provide an overview of subject matter of the present patent application. It is not intended to provide an exclusive or exhaustive explanation of the disclosure. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
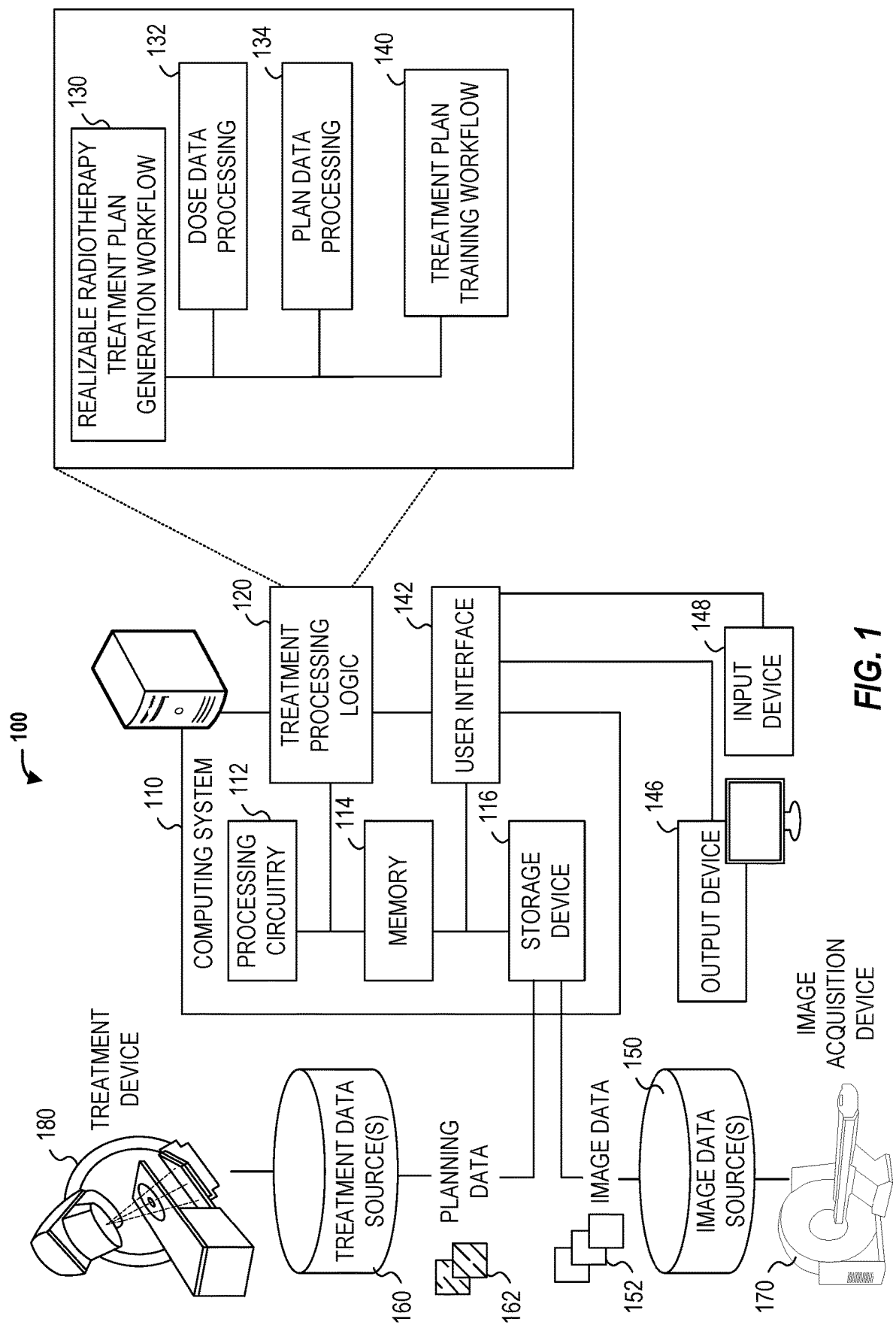
FIG. 1 illustrates an exemplary radiotherapy system adapted for performing treatment plan generation processing, according to some examples.

The present disclosure includes various techniques to improve and enhance realizable radiotherapy treatment plan generation by using a machine learning (ML) technique that has been trained based on prior radiotherapy treatment plans and realizable parameters. The technical advantages include reduced computing processing times to generate realizable radiotherapy treatment plans and accompanying improvements in processing, memory, and network resources used to generate and enhance realizable radiotherapy treatment plans. These improved realizable radiotherapy treatment plans may be applicable to a variety of medical treatment and diagnostic settings or radiotherapy treatment equipment and devices. Accordingly, in addition to these technical benefits, the present techniques may also result in many apparent medical treatment benefits (including improved accuracy of radiotherapy treatment, reduced exposure to unintended radiation, and the like).

The present disclosure is about training an ML technique to automatically generate a radiotherapy treatment plan using training data that includes both how previous estimated treatment parameters of a given type (e.g., dose or machine configuration) were generated and what the realizable version of the estimated parameters ended up being. Prior approaches trained an ML technique to simply estimate treatment parameters without also considering what the realizable parameters ended up being. This required a two-step approach: the first step used the ML technique to estimate a treatment parameter to achieve a treatment goal, and the next step required finding realizable parameters that could achieve the estimated treatment goal. Because the first step does not consider what is actually realizable (e.g., what the radiotherapy equipment or device can actually and physically perform or process), an additional second step is required to find corresponding realizable parameters, resulting in a degradation of the estimated plan's quality and requiring further computational resources.

The present disclosure uses training data to train an ML technique to estimate the treatment parameters in a way that also considers the realizable parameters together. It does so by solving an optimization problem (e.g., using bilevel optimization) using a set of training data that estimates the parameters of a treatment plan to achieve a treatment goal (e.g., a dose distribution) and the actual realizable plan that was generated for that treatment goal. Namely, training data includes a relationship between (e.g., pairs of) a treatment goal (or an inferred treatment goal) determined from (e.g., one or more Magnetic Resonance (MR) images) and one or more plan parameters (e.g., dose). It also includes the realizable treatment plan used to realize the treatment goal. The ML technique is trained by considering the relationship between the generated treatment plan and the realizable treatment plan and considering estimated plan parameters for the treatment goal or an inferred treatment goal. Particularly, the ML technique may infer a treatment goal and obtain training data (including paired data for the inferred treatment goal and the estimated and realizable plan parameters) associated with the inferred treatment goal. The ML technique is trained to estimate the realizable parameters based on the training data associated with the inferred treatment goal. This makes the ML technique, when applied to a new set of data determined to correspond to the inferred treatment goal, generate treatment plan parameters that more closely resemble the realizable treatment plan parameters and increases the overall efficiency and accuracy of automated treatment plan generation. As referred to herein, a "realizable" treatment plan refers to a treatment plan that is compatible with a given radiotherapy system or device and is capable of being performed within the physical constraints of the radiotherapy system or device (e.g., satisfies or meets the physical constraints of the radiotherapy system or device). As referred to herein, an "unrealizable" or "non-realizable" treatment plan refers to a treatment plan that is incompatible with a given radiotherapy system or device and is incapable of being performed within the physical constraints of the radiotherapy system or device (e.g., fails to satisfy or meet the physical constraints of the radiotherapy system of device).

FIG. 1 illustrates an exemplary radiotherapy system 100 adapted to perform radiotherapy plan processing operations using one or more of the approaches discussed herein. These radiotherapy plan processing operations are performed to enable the radiotherapy system to provide radiation therapy to a patient based on specific aspects of captured medical imaging data and therapy dose calculations or radiotherapy machine configuration parameters. Specifically, the following processing operations may be implemented as part of a realizable radiotherapy treatment plan generation workflow 130 and a treatment plan training workflow 140, implemented by treatment processing logic 120. It will be understood, however, that many variations and use cases of the following trained models and treatment processing logic 120 may be provided, including in data verification, visualization, and other medical evaluative and diagnostic settings.

The radiotherapy system 100 includes a radiotherapy processing computing system 110 which hosts treatment processing logic 120. The radiotherapy processing computing system 110 may be connected to a network (not shown), and such network may be connected to the Internet. For instance, a network can connect the radiotherapy processing computing system 110 with one or more medical information sources (e.g., a radiology information system (RIS), a medical record system (e.g., an electronic medical record (EMR)/electronic health record (EHR) system), an oncology information system (OIS)), one or more image data sources 150, an image acquisition device 170 (e.g., an imaging modality), a treatment device 180 (e.g., a radiation therapy device), and a treatment data source 160. As an example, the radiotherapy processing computing system 110 can be configured to receive a treatment goal of a subject (e.g., from one or more MR images) and generate a realizable radiotherapy treatment plan by executing instructions or data from the treatment processing logic 120, as part of operations to generate realizable treatment plans to be used by the treatment device 180 and/or for output on device 146.

The radiotherapy processing computing system 110 may include processing circuitry 112, memory 114, a storage device 116, and other hardware and software-operable features such as a user interface 142, a communication interface (not shown), and the like. The storage device 116 may store transitory or non-transitory computer-executable instructions, such as an operating system, radiation therapy treatment plans (e.g., training data, such as paired prior patient treatment goals and estimated treatment plan parameters, paired prior patient treatment goals and realizable treatment plan parameters, and/or paired prior estimated treatment plan parameters and prior generated realizable treatment plan parameters, and the like), software programs (e.g., image processing software, image or anatomical visualization software, artificial intelligence (AI) or ML implementations and algorithms such as provided by deep learning models, ML models, and neural networks (NNs), etc.), and any other computer-executable instructions to be executed by the processing circuitry 112.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 112 may also be implemented by one or more special-purpose processing devices such as an application specific integrated circuit (ASIC), a field programmable gate array (FPGA), a digital signal processor (DSP), a System on a Chip (SoC), or the like.

As would be appreciated by those skilled in the art, in some examples, the processing circuitry 112 may be a special-purpose processor, rather than a general-purpose processor. The processing circuitry 112 may include one or more known processing devices, such as a microprocessor from the Pentium™ Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processing circuitry 112 may also include graphical processing units such as a GPU from the GeForce®, Quadro®, Tesla® family manufactured by Nvidia™ GMA, Iris™ family manufactured by Intel™, or the Radeon™ family manufactured by AMD™. The processing circuitry 112 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one physical (circuitry based) or software based processor (for example, a multi-core design or a plurality of processors each having a multi-core design). The processing circuitry 112 can execute sequences of transitory or non-transitory computer program instructions, stored in memory 114, and accessed from the storage device 116, to perform various operations, processes, and methods that will be explained in greater detail below. It should be understood that any component in system 100 may be implemented separately and operate as an independent device and may be coupled to any other component in system 100 to perform the techniques described in this disclosure.

The memory 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including images, training data, ML technique parameters, data, or transitory or non-transitory computer executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a transitory or non-transitory machine-readable medium on which is stored one or more sets of transitory or non-transitory instructions and data structures (e.g., software) embodying or utilized by any one or more of the methodologies or functions described herein (including, in various examples, the treatment processing logic 120 and the user interface 142). The instructions may also reside, completely or at least partially, within the memory 114 and/or within the processing circuitry 112 during execution thereof by the radiotherapy processing computing system 110, with the memory 114 and the processing circuitry 112 also constituting transitory or non-transitory machine-readable media.

The memory device 114 and the storage device 116 may constitute a non-transitory computer-readable medium. For example, the memory device 114 and the storage device 116 may store or load transitory or non-transitory instructions for one or more software applications on the computer-readable medium. Software applications stored or loaded with the memory device 114 and the storage device 116 may include, for example, an operating system for common computer systems as well as for software-controlled devices. The radiotherapy processing computing system 110 may also operate a variety of software programs comprising software code for implementing the treatment processing logic 120 and the user interface 142. Further, the memory device 114 and the storage device 116 may store or load an entire software application, part of a software application, or code or data that is associated with a software application, which is executable by the processing circuitry 112. In a further example, the memory device 114 and the storage device 116 may store, load, and manipulate one or more radiation therapy treatment plans, imaging data, segmentation data, treatment visualizations, histograms or measurements, AI model data (e.g., weights and parameters), training data, labels and mapping data, and the like. It is contemplated that software programs may be stored not only on the storage device 116 and the memory 114 but also on a removable computer medium, such as a hard drive, a computer disk, a CD-ROM, a DVD, a Blu-Ray DVD, USB flash drive, a SD card, a memory stick, or any other suitable medium; such software programs may also be communicated or received over a network.

Although not depicted, the radiotherapy processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a IEEE 802.11/Wi-Fi adapter), a telecommunication adapter (e.g., to communicate with 3G, 4G/LTE, and 5G, networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, network may be a LAN or a WAN that may include other systems (including additional image processing computing systems or image-based components associated with medical imaging or radiotherapy operations).

In an example, the radiotherapy processing computing system 110 may obtain image data 152 from the image data source 150 (e.g., MR images) for hosting on the storage device 116 and the memory 114. In yet another example, the software programs may substitute functions of the patient images such as signed distance functions or processed versions of the images that emphasize some aspect of the image information.

In an example, the radiotherapy processing computing system 110 may obtain or communicate image data 152 from or to image data source 150. In further examples, the treatment data source 160 receives or updates the planning data as a result of a realizable treatment plan generated by the realizable radiotherapy treatment plan generation workflow 130. The image data source 150 may also provide or host the imaging data for use in the treatment plan training workflow 140.

In an example, computing system 110 may generate pairs of prior patient treatment goals and estimated treatment plan parameters; prior patient treatment goals and realizable treatment plan parameters; and/or paired prior estimated treatment plan parameters and prior generated realizable treatment plan parameters by communicating with treatment data source 160 and input device 148. For example, computing system 110 may receive input from input device 148 specifying a treatment goal for a given patient and may communicate with treatment processing logic 120 to obtain the estimated treatment plan parameters generated for that treatment goal. This relationship is stored as a set of training data. Additionally, the computing system 110 may receive input from input device 148 specifying the realizable treatment plan parameters for the given treatment goal and may store this relationship as another set of training data. Additionally or alternatively, the computing system 110 may receive input from the input device 148 specifying the estimated treatment plan parameters generated for the given treatment goal and the corresponding realizable parameters of the treatment plan that were generated and store this relationship as another set of training data. Computing system 110 may continue generating such pairs of training data for treatment goals and realizable treatment plans until a threshold number of pairs are obtained.

The processing circuitry 112 may be communicatively coupled to the memory 114 and the storage device 116, and the processing circuitry 112 may be configured to execute computer executable instructions stored thereon from either the memory 114 or the storage device 116. The processing circuitry 112 may execute instructions to cause medical images from the image data 152 to be received or obtained in memory 114 and processed using the treatment processing logic 120.

In addition, the processing circuitry 112 may utilize software programs to generate intermediate data such as updated parameters to be used, for example, by a NN model, machine learning model, realizable radiotherapy treatment plan generation workflow 130, treatment plan training workflow 140, or other aspects involved with generation of a realizable treatment plan as discussed herein. Further, such software programs may utilize the treatment processing logic 120 to implement the realizable radiotherapy treatment plan generation workflow 130 to produce new or updated realizable treatment plans for deployment to the treatment data source 160 and/or presentation on output device 146, using the techniques further discussed herein. The processing circuitry 112 may subsequently then transmit the new or updated realizable treatment plans via a communication interface and the network to the treatment device 180, where the radiation therapy plan will be used to treat a patient with radiation via the treatment device 180, consistent with results of the workflow 130 as trained with the workflow 140. Other outputs and uses of the software programs and the workflows 130, 140 may occur with use of the radiotherapy processing computing system 110.

In the examples herein, the processing circuitry 112 may execute software programs that invoke the treatment processing logic 120 to implement functions of ML, deep learning, NNs, and other aspects of artificial intelligence for realizable treatment plan generation from a treatment goal (e.g., an input MR image or dose information). For instance, the processing circuitry 112 may execute software programs that train, analyze, predict, evaluate, and generate a realizable treatment plan from a received treatment goal (e.g., an MR image or dose information) as discussed herein.

In an example, the image data 152 may include one or more MRI image (e.g., 2D MRI, 3D MRI, 2D streaming MRI, 4D MRI, 4D volumetric Mill, 4D cine MRI, etc.), functional MRI images (e.g., fMRI, DCE-MRI, diffusion MRI), Computed Tomography (CT) images (e.g., 2D CT, 2D Cone beam CT, 3D CT, 3D CBCT, 4D CT, 4DCBCT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer generated synthetic images (e.g., pseudo-CT images) and the like. Further, the image data 152 may also include or be associated with medical image processing data (for example, training images, ground truth images, contoured images, and dose images). In other examples, an equivalent representation of an anatomical area may be represented in non-image formats (e.g., coordinates, mappings, etc.).

In an example, the image data 152 may be received from the image acquisition device 170 and stored in one or more of the image data sources 150 (e.g., a Picture Archiving and Communication System (PACS), a Vendor Neutral Archive (VNA), a medical record or information system, a data warehouse, etc.). Accordingly, the image acquisition device 170 may comprise a MRI imaging device, a CT imaging device, a PET imaging device, an ultrasound imaging device, a fluoroscopic device, a SPECT imaging device, an integrated Linear Accelerator and MRI imaging device, CBCT imaging device, or other medical imaging devices for obtaining the medical images of the patient. The image data 152 may be received and stored in any type of data or any type of format (e.g., in a Digital Imaging and Communications in Medicine (DICOM) format) that the image acquisition device 170 and the radiotherapy processing computing system 110 may use to perform operations consistent with the disclosed embodiments. Further, in some examples, the models discussed herein may be trained to process the original image data format or a derivation thereof.

In an example, the image acquisition device 170 may be integrated with the treatment device 180 as a single apparatus (e.g., a MRI device combined with a linear accelerator, also referred to as an "MRI-Linac"). Such an MRI-Linac can be used, for example, to determine a location of a target organ or a target tumor in the patient so as to direct radiation therapy accurately according to the radiation therapy treatment plan to a predetermined target. For instance, a radiation therapy treatment plan may provide information about a particular radiation dose to be applied to each patient. The radiation therapy treatment plan may also include other radiotherapy information, such as beam angles, dose-histogram-volume information, the number of radiation beams to be used during therapy, the dose per beam, and the like. In some examples, the ML technique trained models in the realizable radiotherapy treatment plan generation workflow 130 are used only to generate a realizable treatment plan, and other workflows or logic (not shown) are used to translate this realizable treatment plan into the specific beam angles and radiation physics used to accomplish the radiotherapy treatment.

The radiotherapy processing computing system 110 may communicate with an external database through a network to send/receive a plurality of various types of data related to image processing and radiotherapy operations. For example, an external database may include machine data (including device constraints) that provides information associated with the treatment device 180, the image acquisition device 170, or other machines relevant to radiotherapy or medical procedures. Machine data information may include radiation beam size, arc placement, beam on and off time duration, machine parameters, segments, multi-leaf collimator (MLC) configuration, gantry speed, MRI pulse sequence, and the like. The external database may be a storage device and may be equipped with appropriate database administration software programs. Further, such databases or data sources may include a plurality of devices or systems located either in a central or a distributed manner.

The radiotherapy processing computing system 110 can collect and obtain data, and communicate with other systems, via a network using one or more communication interfaces, which are communicatively coupled to the processing circuitry 112 and the memory 114. For instance, a communication interface may provide communication connections between the radiotherapy processing computing system 110 and radiotherapy system components (e.g., permitting the exchange of data with external devices). For instance, the communication interface may, in some examples, have appropriate interfacing circuitry from an output device 146 or an input device 148 to connect to the user interface 142, which may be a hardware keyboard, a keypad, or a touch screen through which a user may input information into the radiotherapy system.

As an example, the output device 146 may include a display device that outputs a representation of the user interface 142 and one or more aspects, visualizations, or representations of the medical images, the treatment plans, and statuses of training, generation, verification, or implementation of such plans. The output device 146 may include one or more display screens that display medical images, interface information, treatment planning parameters (e.g., contours, dosages, beam angles, labels, maps, etc.), treatment plans, a target, localizing a target and/or tracking a target, or any related information to the user. The input device 148 connected to the user interface 142 may be a keyboard, a keypad, a touch screen or any type of device that a user may use to the radiotherapy system. Alternatively, the output device 146, the input device 148, and features of the user interface 142 may be integrated into a single device such as a smartphone or tablet computer (e.g., Apple iPad®, Lenovo Thinkpad®, Samsung Galaxy®, etc.).

Furthermore, any and all components of the radiotherapy system may be implemented as a virtual machine (e.g., via VMWare, Hyper-V, and the like virtualization platforms) or independent devices. For instance, a virtual machine can be software that functions as hardware. Therefore, a virtual machine can include at least one or more virtual processors, one or more virtual memories, and one or more virtual communication interfaces that together function as hardware. For example, the radiotherapy processing computing system 110, the image data sources 150, or like components, may be implemented as a virtual machine or within a cloud-based virtualization environment.

The image acquisition device 170 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an example, the image acquisition device 170 can acquire a 2D slice in any orientation. For example, an orientation of the 2D slice can include a sagittal orientation, a coronal orientation, or an axial orientation. The processing circuitry 112 can adjust one or more parameters, such as the thickness and/or orientation of the 2D slice, to include the target organ and/or target tumor. In an example, 2D slices can be determined from information such as a 3D CBCT or CT or MRI volume. Such 2D slices can be acquired by the image acquisition device 170 in "near real-time" while a patient is undergoing radiation therapy treatment (for example, when using the treatment device 180 (with "near real-time" meaning acquiring the data in at least milliseconds or less)).

The treatment processing logic 120 in the radiotherapy processing computing system 110 is depicted as implementing realizable radiotherapy treatment plan generation workflow 130, which involves the use of a trained (learned) ML model. This ML model may be provided by a NN trained as part of a NN model. In an example, the plan generation workflow 130 operated by the treatment processing logic 120 integrates with dose data processing 132 and plan data processing 134 to generate realizable treatment plans based on the paired prior treatment goals and prior realizable treatment plan parameters used in training.

Machine learning CML) algorithms or techniques can be summarized as function approximation. Training data consisting of input-output pairs of some type (e.g., CT-images with segmentations) are acquired from, e.g., expert clinicians and a function is "trained" to approximate this mapping. Some methods involve NNs. In these, a set of parametrized functions $A_\theta$ are selected, where $\theta$ is a set of parameters (e.g., convolution kernels and biases) that are selected by minimizing the average error over the training data. If the input-output pairs are denoted by $(x_m, y_m)$, the function can be formalized by solving a minimization problem such as Equation 1:

$$\min_\theta \sum_{m=1}^{M} \|A_\theta(x_m) - y_m\|^2 \quad (1)$$

Once the network has been trained (e.g., $\theta$ has been selected), the function $A_\theta$ can be applied to any new input. For example, in the above setting of segmentation of CT images, a never before seen CT image can be fed into $A_\theta$, and a segmentation is estimated that matches what an expert clinician would find.

Simple NNs consist of an input layer, a middle or hidden layer, and an output layer, each containing computational units or nodes. The hidden layer(s) nodes have input from all the input layer nodes and are connected to all nodes in the output layer. Such a network is termed "fully connected." Each node communicates a signal to the output node depending on a nonlinear function of the sum of its inputs. For a classifier, the number of input layer nodes typically equals the number of features for each of a set of objects being sorted into classes, and the number of output layer nodes is equal to the number of classes. A network is trained by presenting it with the features of objects of known classes and adjusting the node weights to reduce the training error by an algorithm called backpropagation. Thus, the trained network can classify novel objects whose class is unknown.

Neural networks have the capacity to discover relationships between the data and classes or regression values, and under certain conditions, can emulate any function $y=f(x)$ including non-linear functions. In ML, an assumption is that the training and test data are both generated by the same data-generating process, $p_{data}$ in which each $\{x_i, y_i\}$ sample is identically and independently distributed (i.i.d.). In ML, the goals are to minimize the training error and to make the difference between the training and test errors as small as possible. Under-fitting occurs if the training error is too large; overfitting occurs when the train-test error gap is too large. Both types of performance deficiency are related to model capacity: large capacity may fit the training data very well but lead to overfitting, while small capacity may lead to underfitting.

Figure 2:
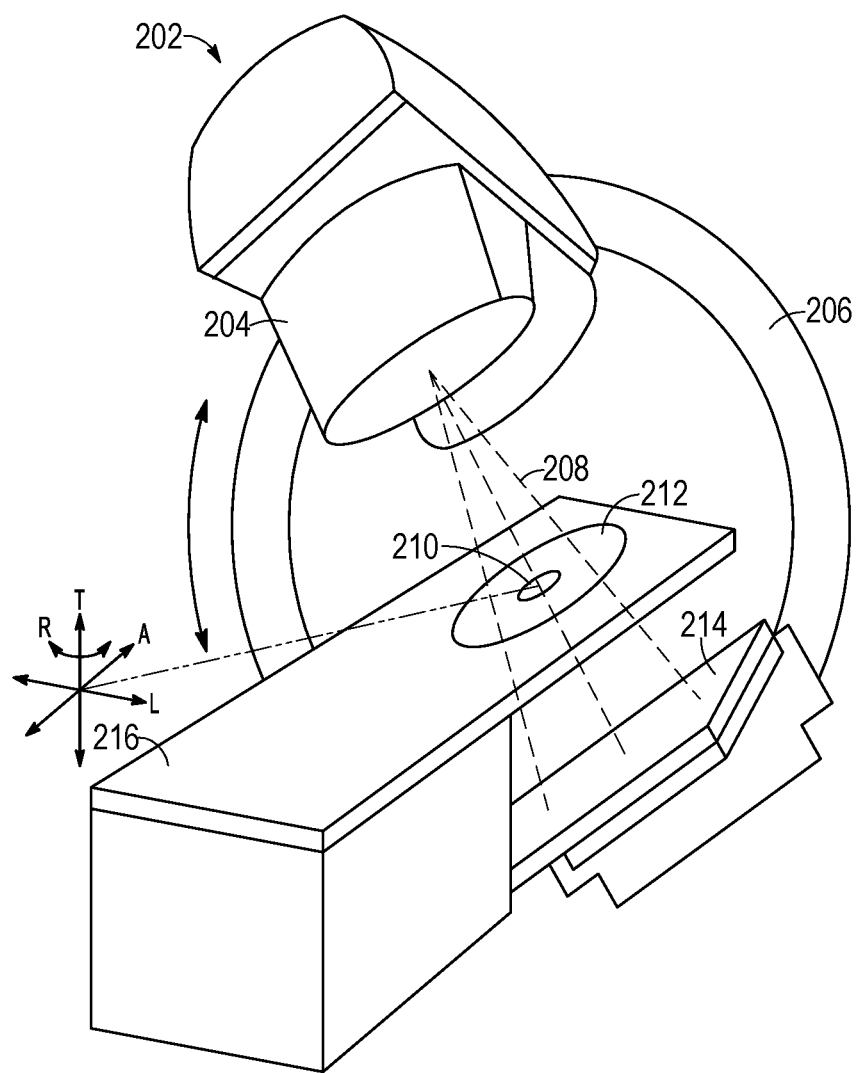
FIG. 2 illustrates an exemplary image-guided radiotherapy device, according to some examples of the disclosure.

FIG. 2 illustrates an exemplary image-guided radiotherapy device 202 that includes a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as a MLC.

As an example, a patient can be positioned in a region 212, supported by the treatment couch 216, to receive a radiation therapy dose according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an example, gantry 206 may be continuously rotatable around couch 216 when the couch 216 is inserted into the treatment area. In another example, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216's movements or rotations in order to properly position the patient in or out of the radiation beam 208, according to a radiation therapy treatment plan. Both the couch 216 and the gantry 206 are independently moveable from one another in multiple degrees of freedom, which allows the patient to be positioned such that the radiation beam 208 can precisely target the tumor.

The coordinate system (including axes A, T, and L) can have an origin located at an isocenter 210. The isocenter 210 can be defined as a location where the central axis of the radiation therapy beam 208 intersects the origin of a coordinate axis, such as to deliver a prescribed radiation dose to a location on or within a patient. Alternatively, the isocenter 210 can be defined as a location where the central axis of the radiation therapy beam 208 intersects the patient for various rotational positions of the radiation therapy output 204 as positioned by the gantry 206 around the axis A.

Gantry 206 may also have an attached imaging detector 214. The imaging detector 214 is preferably located opposite to the radiation source (output 204) and, in an example, the imaging detector 214 can be located within a field of the therapy beam 208. The imaging detector 214 can be mounted on the gantry 206, preferably opposite the radiation therapy output 204, so as to maintain alignment with the radiation beam 208. The imaging detector 214 rotates about the rotational axis as the gantry 206 rotates. In an example, the imaging detector 214 can be a flat panel detector (e.g., a direct detector or a scintillator detector). In this manner, the imaging detector 214 can be used to monitor the radiation beam 208, or the imaging detector 214 can be used for imaging the patient's anatomy, such as portal imaging. The control circuitry of radiation therapy device 202 may be integrated within the radiotherapy system 100 or remote from it.

In an illustrative example, one or more of the couch 216, the therapy output 204, or the gantry 206 can be automatically positioned, and the therapy output 204 can establish the therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially but can intersect in a desired therapy locus on or within the patient, such as at the isocenter 210. A prescribed cumulative dose of radiation therapy can thereby be delivered to the therapy locus while damage to tissue nearby the therapy locus can be reduced or avoided.

Thus, FIG. 2 specifically illustrates an example of a radiation therapy device 202 operable to provide radiotherapy treatment to a patient consistent with or according to a realizable radiotherapy treatment plan, with a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient. In another example, a radiation therapy device can be a combination of a linear accelerator and an image acquisition device. In some examples, the image acquisition device may be an MRI, an X-ray, a CT, a CBCT, a spiral CT, a PET, a SPECT, an optical tomography, a fluorescence imaging, ultrasound imaging, or radiotherapy portal imaging device, and the like, as would be recognized by one of ordinary skill in the art.

As discussed above, the training data used by treatment processing logic 120 may include a plurality of previous estimated treatment plans paired with prior treatment goals that are stored in a memory 114. For example, the stored training data may include diagnostic images, treatment images (dose maps), segmentation information, and the like, associated with one or more previous estimated treatment plans. The training data may include a plurality of training samples. Each training sample may comprise a feature vector and a corresponding output vector.

The feature vector may include one or more feature elements. Each feature element may indicate an observation of a medical image (e.g., provided by image acquisition device 140) used in a past radiotherapy session. The observation may be a distance between a volume (e.g., a voxel) and an anatomical region, such as a target or the surface of the body part in the medical image. In another example, the observation may include spatial coordinates of an anatomical region or a probability that an anatomical region includes a particular tissue type. In another example, the feature element may include patient specific information, responsible physician, organ or volume of interest segmentation data, functional organ modeling data (e.g., serial versus parallel organs, and appropriate dose response models), radiation dosage (e.g., also including DVH information), lab data (e.g., hemoglobin, platelets, cholesterol, triglycerides, creatinine, sodium, glucose, calcium, weight), vital signs (blood pressure, temperature, respiratory rate and the like), genomic data (e.g., genetic profiling), demographics (age, sex), other diseases affecting the patient (e.g., cardiovascular or respiratory disease, diabetes, radiation hypersensitivity syndromes and the like), medications and drug reactions, diet and lifestyle (e.g., smoking or non-smoking), environmental risk factors, tumor characteristics (histological type, tumor grade, hormone and other receptor status, tumor size, vascularity cell type, cancer staging, gleason score), previous treatments (e.g., surgeries, radiation, chemotherapy, hormone therapy), lymph node and distant metastases status, genetic/protein biomarkers (e.g., such as MYC, GADD45A, PPM1D, BBC3, CDKN1A, PLK3, XPC, AKT1, RELA, BCL2L1, PTEN, CDK1, XIAP, and the like), single nucleotide polymorphisms (SNP) analysis (e.g., XRCC1, XRCC3, APEX1, MDM2, TNFR, MTHFR, MTRR, VEGF, TGFβ, TNFα), and the like. The feature vector may include one or more such feature elements, regardless of whether these feature elements are related to each other or not.

The output vector may include one or more output elements. Each output element may indicate a corresponding estimated plan outcome or parameter in the past radiotherapy session based on the observation(s) included in the feature vector. For example, the output element may include the estimated dose applied or received at a particular spatial location (e.g., a voxel). In another example, the output element may include a patient survival time based on observations such as a treatment type, treatment parameters, patient history, and/or patient anatomy. Additional examples of output elements include, but not limited to, a normal tissue complication probability (NTCP), a region displacement probability during treatment, or a probability that a set of coordinates in a reference image is mapped to another set of coordinates in a target image. The output vector may include one or more such output elements, regardless of whether these output elements are related to each other or not.

As an example of an embodiment, an output element may include a dose to be applied to a voxel of a particular OAR. Further, a feature element may be used to determine the output element. The feature element may include a distance between the voxel in the OAR and the closest boundary voxel in a target tumor. Therefore, the feature element may include a signed distance x indicating the distance between a voxel in an OAR and the closest boundary voxel in a target for the radiation therapy. The output element may include a dose D in the voxel of the OAR from which x is measured. In some other embodiments, each training sample may correspond to a particular voxel in the target or OAR, such that multiple training samples within the training data correspond to the whole volume of the target or OAR and other anatomical portions subject to the radiotherapy treatment.

Additional training data may include further pairs of realizable treatment plan parameters corresponding to certain input parameters (e.g., training goals and/or estimated treatment plan parameters). Specifically, this additional training data may relate the actual realizable parameters for a given prior training goal or estimated treatment plan parameters in the output vector. In some cases, whereas the output vector may specify parameters of a treatment plan that are not realizable (e.g., cannot be performed or achieved with a given radiotherapy device), the realizable treatment plan parameters specify the corresponding treatment plan parameters that can be realizable or performed by the given radiotherapy device.

In treatment planning, a clinical decision maker wrestles with the physical limitations of the radiotherapy equipment in a struggle to find an acceptable compromise for the patient. This acceptable compromise results in a realizable treatment plan. In most cases this interaction is mediated by an optimization problem. The overall structure of these optimization problems is the same for most forms of radiotherapy, including linac based treatments (3D-CRT, IMRT, VMAT), proton treatments, Gamma Knife radiosurgery and brachytherapy. The disclosed techniques are applicable to all of different forms of radiotherapy.

The biological effect of the radiotherapy treatment depends on the absorbed dose d. The radiotherapy equipment differ in the way they deliver the dose, but the relationship can usually be modeled (at least approximately) as a linear function $d(x)=\Phi x$, where $\Phi$ is a dose influence matrix that maps from the decision variables x to dose. Typically, the objective function $f$ and at least some of the constraints $c_i$ are formulated only in terms of dose. The physical meaning of the decision variables depends on the treatment modality. For example, the decision variables include irradiation time in Gamma Knife radiosurgery and brachytherapy whereas the decision variables include fluence in linac treatments. Commonly, both the elements in the dose influence matrix and the decision variables are non-negative.

The dose influence matrix $\Phi$ is often static during the optimization, which means that it could be precomputed and stored. A typical optimization problem in radiotherapy thus has the form of Equation (2):

$$\underset{x,d}{\text{minimize}} f(d) \quad (2)$$
$$\text{subject to} \quad d = \Phi x,$$
$$x \geq 0,$$
$$c_i(x) \leq 0, \quad i \in C_x$$
$$c_i(d) \leq 0, \quad i \in C_d$$

where $C_x$ and $C_d$ denote the set of machine constraints and dose constraints, respectively. However, which constraint functions {ci} are relevant depends on the application. The functions $f$ and ci can be both nonlinear and non-convex (or even integer valued). Two examples of complicated optimization problems arise from isocenter selection in Gamma Knife radiosurgery or arc sequencing in VMAT planning. In such cases, the optimization problem can be attacked either directly (e.g., by direct aperture optimization in VMAT planning) or indirectly (e.g., via a sequence of increasingly difficult subproblems). Regardless, the most complex optimization problem typically dominates the total runtime. The disclosed techniques cover all the cases and thus the disclosed techniques formulate an optimization problem in the general form using Equation (3):

$$\underset{x}{\text{minimize}} \quad f(x) \quad (3)$$
$$\text{subject to} \quad x \in \Omega,$$

for some general feasible set $\Omega$.

The disclosed techniques cover multiple different embodiments, that may be combined, provided by the treatment processing logic 120 to automatically generate a realizable treatment plan. In some embodiments, machine parameters are estimated or predicted and those parameters are then projected onto a set of realizable treatment plans. For example, treatment processing logic 120 begins by predicting some property of the treatment plan (for example, the machine parameters or the dose map). Treatment processing logic 120 then finds the realizable treatment plan that most accurately achieves this property. For example, treatment processing logic 120 first uses a machine learning technique to predict the decision variables $\hat{x}=\hat{A}_\theta(u)\in X$. These decision variables are not necessarily realizable, and thus treatment processing logic 120 projects them onto the feasible set $\Omega$ by solving Equation 4:

$$\underset{x\in\Omega}{\text{minimize}} \|x - \hat{x}\|_2^2 \quad (4)$$

If $\Omega$ is convex, the projection operator given above is convex and has Lipschitz constant one. It is therefore differentiable almost everywhere and can be back-propagated allowing treatment processing logic 120 to train the ML technique using any loss function.

In particular, the treatment processing logic 120 may be configured to train the ML technique $\hat{A}_\theta(u)$ in accordance with Equation 5:

$$\hat{A}_\theta(u)\theta^* = \underset{\theta\in\Theta}{\text{argmin}} E_{u,\hat{x}}\left[\left\|\hat{x} - \left(\underset{x\in\Omega}{\text{argmin}} \|x - \hat{A}_\theta(u)\|_2^2\right)\right\|_2^2\right] \quad (5)$$

Specifically, the ML technique in this embodiment is trained using bilevel optimization. A first loss function is used to train $\hat{A}_\theta(u)$ based on a deviation between the realizable decision variables x and application of the $\hat{A}_\theta(u)$ to a given prior patient's treatment goal u. A second loss function is used to train $\hat{A}_\theta(u)$ based on a deviation between a result of minimizing the first loss function (e.g., estimated decision variables for the given patient's treatment goal u) and estimated decision variables $\hat{x}$. In this way, after the ML technique $\hat{A}_\theta(u)$ is trained, during evaluation for a new patient treatment goal u, the treatment processing logic 120 may be configured to generate decision variables for a treatment plan in accordance with Equation 6:

$$x^* = \underset{x\in\Omega}{\text{argmin}} \|x - \hat{A}_{\theta_*}(u)\|_2^2 \quad (6)$$

In some embodiments, a dose distribution is predicted or estimated using a data-driven process (e.g., a NN) and then that dose distribution is projected onto a set of realizable treatment plans. Treatment processing logic 120 uses a machine learning technique $\hat{A}_\theta$ to predict a vector $\hat{d}=\hat{A}_\theta(u)$ of doses in each voxel. This dose distribution is not necessarily realizable in that there does not necessarily exist $x \in \Omega$ such that $\Phi_x = \hat{d}$. To find a realizable plan, treatment processing logic 120 picks the $x \in \Omega$ that gives a dose plan that is closest to d in accordance with Equation 7, $$\underset{x \in \Omega}{\text{minimize}} \|\Phi x - \hat{d}\|_2^2 \tag{7}$$

where $\Phi$ is a matrix (e.g., the dose influence matrix) that maps from the decision variables x to dose d. If $\Omega$ is convex, Equation 7 is uniquely solvable and the solution operator is $\|\Phi^\dagger\|$ Lipschitz making it differentiable. If the decision variables, e.g., fluences (in fluence map optimization) or irradiation times (in Gamma Knife radiosurgery or brachytherapy), are non-negative, the projection step can be phrased as a non-negative least-squares problem. The treatment processing logic 120 trains the machine learning technique $\hat{A}_\theta$ using any loss function. In some implementations, the loss function is the $L_2$-loss between the dose distribution in the training data and the projected (estimated) dose distribution. In such circumstances, the training problem is characterized by Equation 8:

$$\theta^* = \underset{\theta \in \Theta}{\text{argmin}}\, E_{u,d}\left[\left\|d - \Phi\left(\underset{x \in \Omega}{\text{argmin}}\|\Phi x - \hat{A}_\theta(u)\|_2^2\right)\right\|_2^2\right] \tag{8}$$

In particular, the treatment processing logic 120 may be configured to train the ML technique $\hat{A}_\theta(u)$ in accordance with Equation 8. Specifically, the ML technique in this embodiment is trained using bilevel optimization. A first loss function is used to train $\hat{A}_\theta(u)$ based on a deviation between the realizable dose distribution $\Phi_x$ and application of the $\hat{A}_\theta(u)$ to a given prior patient's treatment goal u. A second loss function is used to train $\hat{A}_\theta(u)$ based on a deviation between a result of minimizing the first loss function (e.g., estimated dose distribution for the given patient's treatment goal u) and estimated dose distribution d. In this way, after the ML technique is trained, during evaluation for a new patient treatment goal u, the treatment processing logic 120 may be configured to generate a dose distribution for a treatment plan in accordance with Equation 9:

$$x^* = \underset{x \in \Omega}{\text{argmin}} \|\Phi x - \hat{A}_{\theta^*}(u)\|_2^2 \tag{9}$$

In some embodiments, a data driven process (e.g., a NN) is employed by treatment processing logic 120 to predict or estimate parameters of an optimization problem (e.g., dose prescriptions), and then the optimization problem is solved to obtain a realizable treatment plan. In particular, the treatment goal parameter u for a given patient may include a dose rate kernel $\Phi$ as well as MR images and corresponding segmentations. The machine learning technique $\hat{A}_\theta(u)$ may output the dose rate kernel $\Phi$, dose distribution over all N voxels that is multivariate Gaussian with mean $\mu_\theta$, and diagonal precision $\Sigma_\theta^{-1}$. A loss function $l_x$ can be utilized such that $l_x(x, \hat{A}_\theta(u)) = \ell_x(x, \{\Phi, \mu_\theta, \Sigma_\theta^{-1}\}) = \|\Phi x - \mu_\theta(u)\|_{\Sigma_\theta^{-1}(u)}^2$ and a second loss function $l_\theta(w, \hat{A}_\theta(u)) = l_\theta(\{\hat{d}, \Phi\}, \hat{A}_\theta(u)) = \|\hat{d} - \Phi \hat{A}_\theta(u)\|_2^2$ is utilized which is the $L_2$-loss between a realizable dose distribution $d_\theta(u) = \Phi \hat{A}_\theta(u)$ and the training data $\hat{d}$. In this case, the optimization problem can be characterized by Equation 10:

$$\theta^* = \underset{\theta \in \Theta}{\text{argmin}} \frac{1}{M} \sum_{m=1}^{M} \left\| \hat{d}_m - \Phi_m\left(\underset{x \geq 0}{\text{argmin}}\|\Phi_m x - \mu_\theta(u_m)\|_{\Sigma^{-1}(u_m)}^2\right)\right\|_2^2 \tag{10}$$

The resulting parameters $\theta^*$ of the ML technique can be used to make predictions using $A_{\theta^*}(u)$.

In some implementations, $u \in U$ may represent some input parameters related to a patient. For example, u may represent medical images, segmentations of an object or region of interest associated with the patient, dose prescriptions, or any other input parameter discussed above. $x \in X$ may denote the parameters used to define a realizable treatment plan. These parameters could be fluence maps, machine parameters (e.g., control points in IMRT/VMAT, or shot configurations and corresponding weights in Gamma Knife radiosurgery) or any other "output" parameter discussed above. In some embodiments, the ML technique $A_\theta$: $U \rightarrow V$ may take raw input parameters as input and output the machine parameters. The machine parameters and their physical constraints may be difficult to represent using common ML techniques. In such cases, the optimization problem may be characterized by Equation 11:

$$A_\theta(u) = \underset{x \in X}{\text{argmin}}\, l_x(x, \hat{A}_\theta(u)) \tag{11}$$

where $\hat{A}_\theta$: $U \rightarrow V$ is the ML technique that maps to the simpler space V and $\ell_x$: $X \times V \rightarrow \mathbb{R}$ is a first loss function.

As an example, $\hat{A}_\theta$ may be the ML technique that returns an estimated dose distribution and x may be selected as the machine parameters that best approximate this dose distribution. Since the dose distribution can be seen as an image, classical convolutional NNs may be employed to represent $\hat{A}_\theta$. Training is performed in order to select the parameter $\theta$ of the ML technique $\hat{A}_\theta$. If M training data is available and the training goal includes minimizing the average $\ell_\theta$ error, the training optimization problem can be characterized by Equation 12:

$$\theta^* = \underset{\theta \in \Theta}{\text{argmin}} \sum_{m=1}^{M} \left[ l_\theta\left(w_m, \underset{x \in X}{\text{argmin}}\, l_x(x, \hat{A}_\theta(u_m))\right)\right] \tag{12}$$

where $W_m \in W$ are some plan characteristics that are used in a second loss function $\ell_\theta$: $W \times X \rightarrow \mathbb{R}$ which may be different from the first loss function to quantify the similarity between the generated plan and a plan in the training data set. This loss function could be fixed a priori (e.g., cross-entropy or $L_2$-loss, or be adapted in the course of the training, such as an adversarial loss).

To train the ML technique using gradient based training methods, the argmin operator can be differentiated (back-propagated)

$$v \rightarrow \underset{x \in X}{\text{argmin}}\, l_x(x, v).$$

Multiple implementations can be employed to perform such training. In some embodiments, explicit differentiation of the argmin operator can be employed. In this method, it can be observed that for a range of the first loss, the argmin operator can be analytically differentiated, which can be used to perform the back-propagation. In another implementation, automatic differentiation of unrolled optimization can be employed. Here, any optimization scheme can be utilized to solve for the argmin operator and unroll a fixed number of steps. The final result can be considered as an approximation to the argmin operator, and automatic differentiation can then be used to compute the derivative of the approximation with respect to u. In another implementation, the argmin operator can be solved for using learned optimization. The argmin operator can be approximated by an appropriately trained NN. For example, the NN $B_\phi$ can be trained to approximate the argmin operator. Either supervised or unsupervised training can be employed. Specifically, supervised training can be employed and characterized by Equation 13:

$$\phi^* = \underset{\phi \in \Phi}{\mathrm{argmin}} E_u \left[ \left\| B_\phi(\hat{A}_\theta(u)) - \underset{x \in X}{\mathrm{argmin}} l_x(x, \hat{A}_\theta x(u)) \right\|_2^2 \right] \quad (13)$$

or unsupervised training can be employed and characterized by Equation 14:

$$\phi^* = \underset{\phi \in \Phi}{\mathrm{argmin}} E_u \left[ l_x \left( B_\phi(\hat{A}_\theta(u)), \hat{A}_\theta(u) \right) \right] \quad (14)$$

Using this network, training can be approximated by Equation 15:

$$\theta^* = \underset{\theta \in \Theta}{\mathrm{argmin}} E_{u,w} \left[ l_\theta \left( w, B_\phi * (x, \hat{A}_\theta(u)) \right) \right] \quad (15)$$

Since the operator $B_\phi$ is given by a NN, the argmin operator can be back-propagated through.

Figure 3:
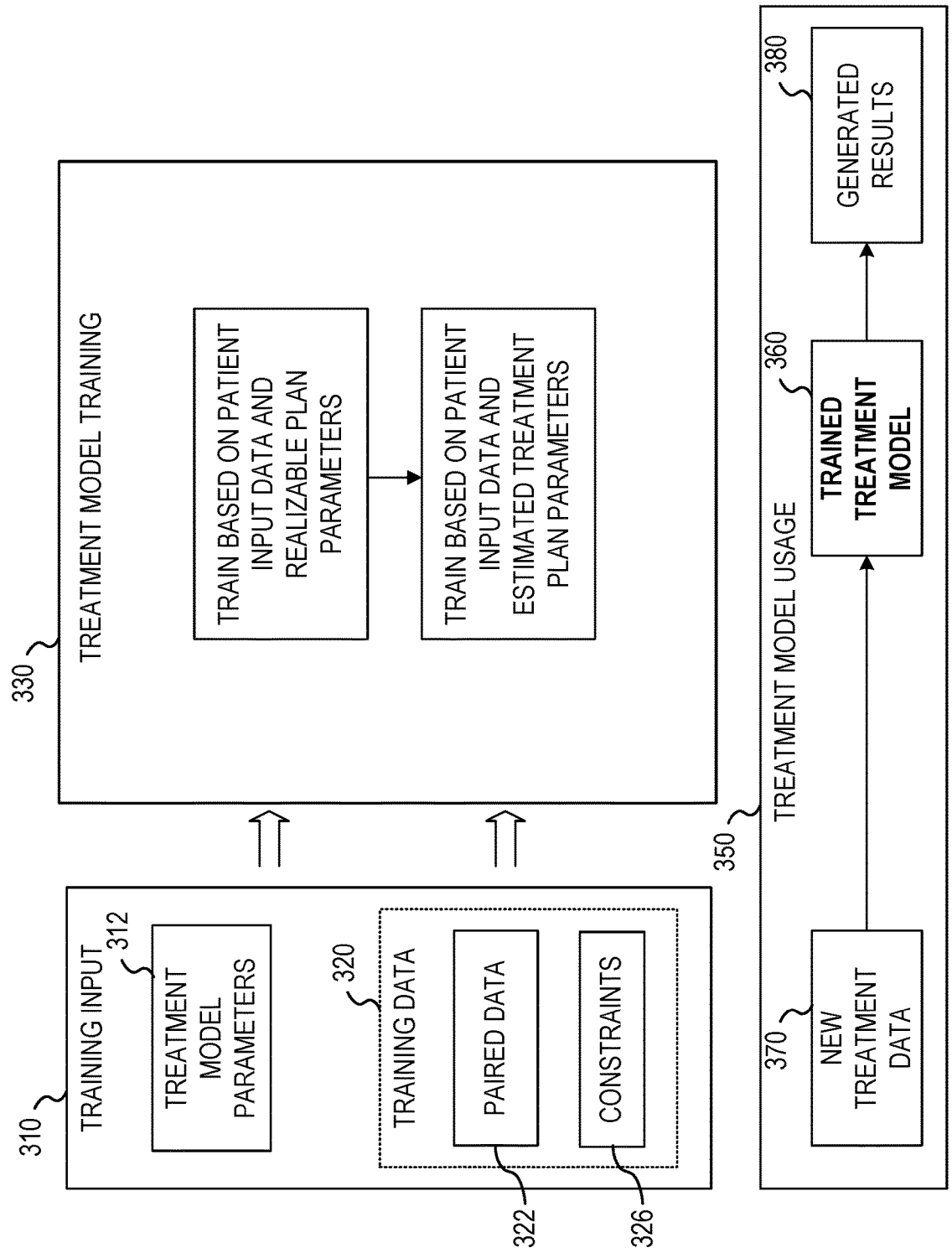
FIG. 3 illustrates an exemplary data flow for training and use of a machine learning technique to generate a realizable radiotherapy treatment plan, according to some examples of the disclosure.

FIG. 3 illustrates an exemplary data flow for training and use of a machine learning technique to generate a realizable radiotherapy treatment plan, according to some examples of the disclosure. The data flow includes training input 310, treatment model (technique) training 330, and treatment model usage 350.

Training input 310 includes treatment model parameters 312 and training data 320 which may include paired training data sets 322 (e.g., input-output training pairs) and constraints 326. Treatment model parameters 312 stores or provides the parameters or coefficients of the machine learning technique $\hat{A}_\theta$. During training, these parameters 312 are adapted based on the input-output training pairs of the training data sets 322. After the parameters 312 are adapted (after training), the parameters are used by a trained treatment model 360 to implement the trained machine learning technique $\hat{A}_\theta$ on a new set of treatment data 370.

Training data 320 includes constraints 326 which may define the physical constraints of a given radiotherapy device. These constraints 326 are used to adapt an estimated set of treatment plan parameters to realizable treatment plan parameters. The paired data 322 may include a first set of input-output pairs, such as a given set of prior patient input parameters (e.g., MR images) and the corresponding estimated treatment plan parameters that were generated. The paired data 322 may include a second set of input-output pairs, such as a given set of prior patient input parameters (e.g., MR images) and the corresponding realizable treatment plan parameters that were generated. The paired data 322 may include a third set of input-output pairs, such as a given set of prior estimated plan parameters (e.g., an estimated dose distribution) and the corresponding realizable treatment plan parameters (e.g., actual dose distributions that take into account constraints 326) that were generated.

Treatment model training 330 trains the machine learning technique $\hat{A}_\theta$ based on the first, second, and/or third sets of input-output pairs of paired data 322. For example, the treatment model training 330 may train the treatment model parameters 312 by minimizing a first loss function based on training patient input data and the corresponding realizable plan parameters and by minimizing a second loss function based on an output of minimizing the first loss function and the training patient input data and the corresponding estimated plan parameters. In some implementations, the two loss functions are minimized in using bilevel optimization. The result of minimizing these loss functions for multiple sets of training data trains, adapts, or optimizes the treatment model parameters 312. Treatment model training 330 may be performed in accordance with any one or combination of Equations 5-8, 10, and 12-15. In this way, the machine learning technique is trained to establish a relationship between the particular type of input parameter and a set of realizable radiotherapy treatment plan parameters to achieve a target radiotherapy dose distribution, selected points from a DVH, or one or more radiobiological properties.

After the machine learning technique $\hat{A}_\theta$ is trained, a new treatment data 370 including one or more patient input parameters (e.g., an MR image, a medical image, segmentation information of an object of interest associated with the patient, or dose prescription information) may be received. The trained machine learning technique $\hat{A}_\theta$ may be applied to the new treatment data 370 to generate generated results 380 including one or more parameters of a realizable radiotherapy treatment plan. In some implementations, the one or more parameters of the realizable treatment plan are further analyzed against constraints 326 to verify and adapt the parameters within the physical constraints of the radiotherapy device. In some implementations, generating the realizable plan parameter includes using at least one of an explicit differentiation process, composition of a fixed number of differentiable iterations, or a differentiable machine learning technique trained to estimate the realizable plan parameter.

Figure 4:
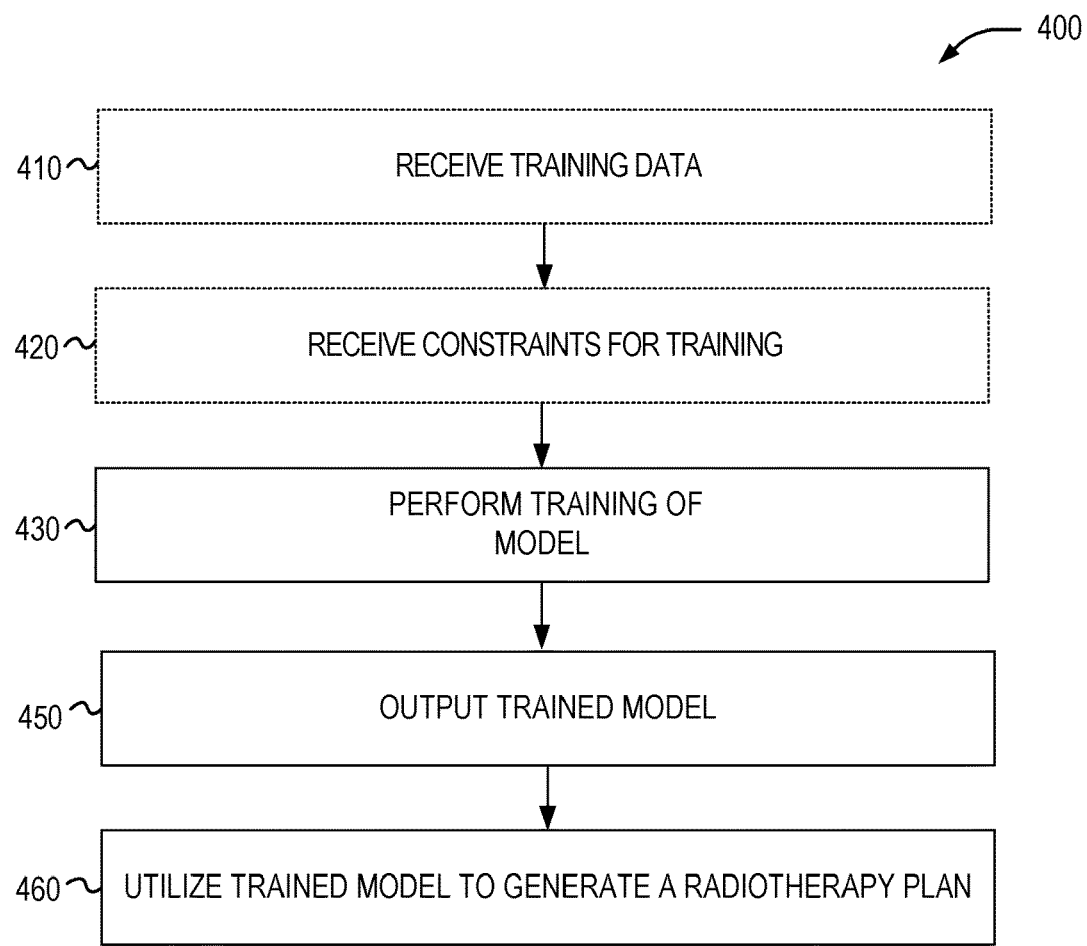
FIGS. 4-6 illustrate flowcharts of exemplary operations for training and using a machine learning technique to generate a realizable radiotherapy treatment plan, according to some examples of the disclosure.

FIG. 4 is a flowchart illustrating example operations of the treatment processing logic 120 in performing process 400, according to example embodiments. The process 400 may be embodied in computer-readable instructions for execution by one or more processors such that the operations of the process 400 may be performed in part or in whole by the functional components of the treatment processing logic 120; accordingly, the process 400 is described below by way of example with reference thereto. However, in other embodiments, at least some of the operations of the process 400 may be deployed on various other hardware configurations. The process 400 is therefore not intended to be limited to the treatment processing logic 120 and can be implemented in whole, or in part, by any other component. Some or all of the operations of process 400 can be in parallel, out of order, or entirely omitted.

At operation 410, treatment processing logic 120 receives training data. For example, treatment processing logic 120 receives training data 320, which may include paired training data sets 322 (e.g., input-output training pairs).

At operation 420, treatment processing logic 120 receives constraints for training the model. For example, treatment processing logic 120 receives constraints 326.

At operation 430, treatment processing logic 120 performs training of the model. For example, treatment processing logic 120 performs bilevel optimization of two loss functions. Illustrative bilevel optimization is shown and described in connection with FIG. 5 below.

At operation 450, treatment processing logic 120 outputs the trained model. For example, treatment processing logic 120 outputs the trained treatment model 360 to operate on a new set of input data 370 to generate a realizable treatment plan.

At operation 460, treatment processing logic 120 utilizes trained model to generate a radiotherapy plan. For example, treatment processing logic 120 utilizes the trained treatment model 360 to operate on a new set of input data 370 to generate a realizable treatment plan.

Figure 5:
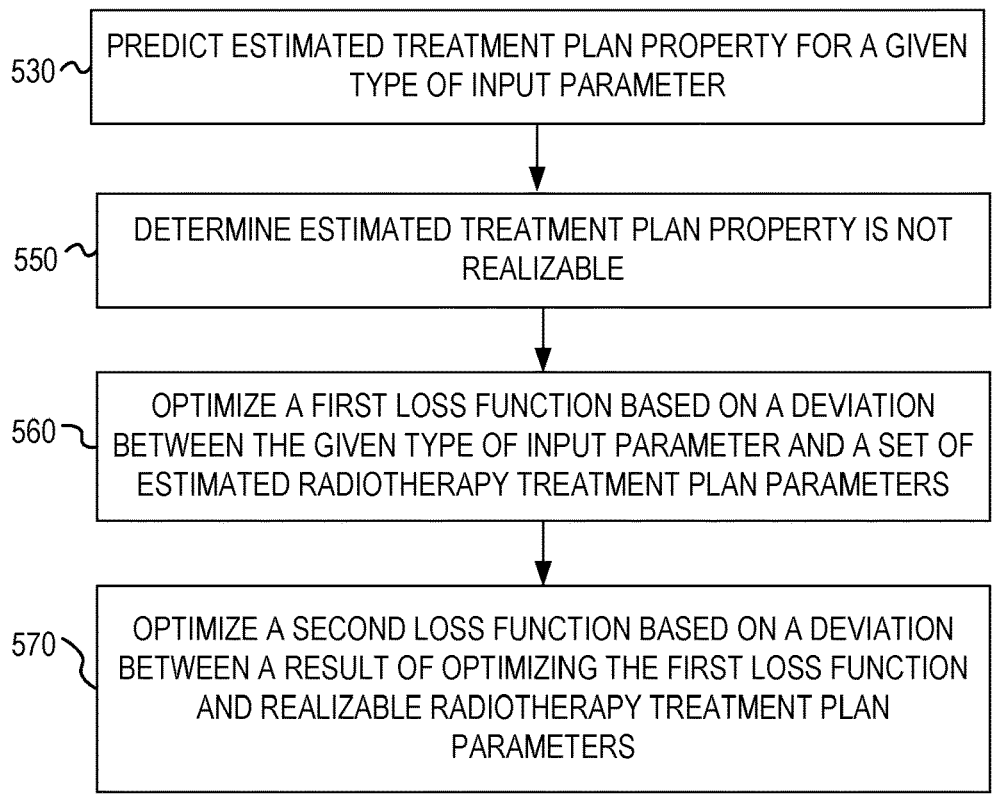

FIG. 5 is a flowchart illustrating example operations of the treatment processing logic 120 in performing process 500, according to example embodiments. The process 500 may be embodied in computer-readable instructions for execution by one or more processors such that the operations of the process 500 may be performed in part or in whole by the functional components of the treatment processing logic 120; accordingly, the process 500 is described below by way of example with reference thereto. However, in other embodiments, at least some of the operations of the process 500 may be deployed on various other hardware configurations. The process 500 is therefore not intended to be limited to the treatment processing logic 120 and can be implemented in whole, or in part, by any other component. Some or all of the operations of process 500 can be in parallel, out of order, or entirely omitted.

At operation 530, treatment processing logic 120 predicts an estimated treatment plan property for a given type of input parameter. For example, treatment processing logic 120 may compute a particular dose distribution for a given MR or medical image of a patient.

At operation 550, treatment processing logic 120 determines that the estimated treatment plan property is not realizable. For example, the treatment processing logic 120 determines that the particular dose distribution fails to meet or satisfy the physical constraints of a given radiotherapy device.

At operation 560, treatment processing logic 120 optimizes a first loss function based on a deviation between the given type of input parameter (e.g., prior patient's treatment goal u) and a set of estimated radiotherapy treatment plan parameters. For example, in Equation 8, treatment processing logic 120 optimizes a first loss function used to train the machine learning technique $\hat{A}_\theta(u)$ based on a deviation between the realizable dose distribution $\Phi_x$ in the training data and application of the machine learning technique $\hat{A}_\theta(u)$ to a given prior patient's treatment goal u in the training data. In some implementations, the first loss function may be optimized based on a deviation between the estimated dose distribution in the training data and application of the machine learning technique to the prior patient's treatment goal u.

At operation 570, treatment processing logic 120 optimizes a second loss function based on a deviation between a result of optimizing the first loss function and realizable radiotherapy treatment plan parameters. For example, in Equation 8, treatment processing logic 120 optimizes a second loss function used to train $\hat{A}_\theta(u)$ based on a deviation between a result of minimizing the first loss function (e.g., estimated dose distribution for the given patient's treatment goal u) and an estimated dose distribution d in the training data. In some implementations, the second loss function may be optimized based on a deviation between the realizable dose distribution in the training data and a result of minimizing the first loss function.

As another example, the treatment processing logic 120 obtains a first set of training data that indicates a training patient's input parameter (e.g., treatment goal), the estimated dose distribution for that patient's input parameter, and the realizable dose distribution for that patient's input parameter. The first loss function may train the machine learning technique based on application of the current parameters of the machine learning technique to the training patient's input parameter and a deviation between application of the current parameters to the training patient's input parameter and the estimated dose distribution for that training input parameter. The first loss function may continue to train the machine learning technique based on application of the current parameters of the machine learning technique to a second training patient's input parameter and a deviation between application of the current parameters to the second training patient's input parameter and the estimated dose distribution for that training input parameter. After a certain number of training steps based on the first loss function, the treatment processing logic 120 may continue to operation 570 to train further based on the second loss function. Specifically, the machine learning technique may be trained based on a second loss function and a deviation between the realizable dose distribution for a first training patient and application of the current parameters to the first training patient's input parameter. The machine learning technique may continue to be trained based on the second loss function and a deviation between the realizable dose distribution for the second training patient and application of the current parameters to the second training patient's input parameter. This bilevel optimization may continue until all of the training patient's training data is used in training and/or after a threshold number of epochs are reached.

Figure 6:
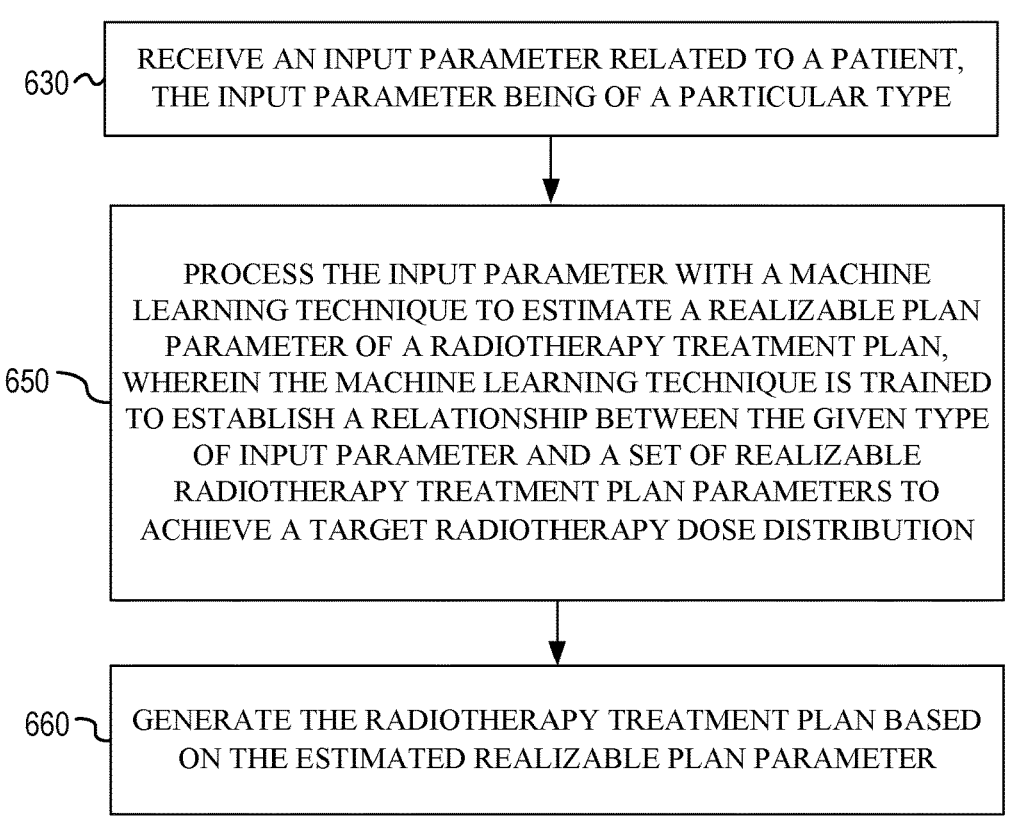

FIG. 6 is a flowchart illustrating example operations of the treatment processing logic 120 in performing process 600, according to example embodiments. The process 600 may be embodied in computer-readable instructions for execution by one or more processors such that the operations of the process 600 may be performed in part or in whole by the functional components of the treatment processing logic 120; accordingly, the process 600 is described below by way of example with reference thereto. However, in other embodiments, at least some of the operations of the process 600 may be deployed on various other hardware configurations. The process 600 is therefore not intended to be limited to the treatment processing logic 120 and can be implemented in whole, or in part, by any other component. Some or all of the operations of process 600 can be in parallel, out of order, or entirely omitted.

At operation 630, treatment processing logic 120 receives an input parameter related to a patient, with the input parameter being of a particular type.

At operation 650, treatment processing logic 120 processes the input parameter with a machine learning technique to estimate a realizable plan parameter of a radiotherapy treatment plan, wherein the machine learning technique is trained to establish a relationship between the given type of input parameter and a set of realizable radiotherapy treatment plan parameters to achieve a target radiotherapy dose distribution.

At operation 660, treatment processing logic 120 generates the radiotherapy treatment plan based on the estimated realizable plan parameter.

As previously discussed, respective electronic computing systems or devices may implement one or more of the methods or functional operations as discussed herein. In one or more embodiments, the radiotherapy processing computing system 110 may be configured, adapted, or used to control or operate the image-guided radiation therapy device 202, perform or implement the training or prediction operations from model 300, operate the trained treatment model 360, perform or implement the operations of the flowcharts for processes 400-600, or perform any one or more of the other methodologies discussed herein (e.g., as part of treatment processing logic 120 and the workflows 130, 140). In various embodiments, such electronic computing systems or devices operates as a standalone device or may be connected (e.g., networked) to other machines. For instance, such computing systems or devices may operate in the capacity of a server or a client machine in server-client network environment, or as a peer machine in a peer-to-peer (or distributed) network environment. Features of computing systems or devices may be embodied by a personal computer (PC), a tablet PC, a Personal Digital Assistant (PDA), a cellular telephone, a web appliance, or any machine capable of executing instructions (sequential or otherwise) that specify actions to be taken by that machine.

As also indicated above, the functionality discussed above may be implemented by instructions, logic, or other information storage on a machine readable medium. While the machine-readable medium may have been described in various examples with reference to be a single medium, the term "machine-readable medium" may include a single medium or multiple media (e.g., a centralized or distributed database, and/or associated caches and servers) that store the one or more transitory or non-transitory instructions or data structures. The term "machine-readable medium" shall also be taken to include any tangible medium that is capable of storing, encoding or carrying transitory or non-transitory instructions for execution by the machine and that cause the machine to perform any one or more of the methodologies of the present disclosure, or that is capable of storing, encoding or carrying data structures utilized by or associated with such instructions.

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, this disclosure also contemplates examples in which only those elements shown or described are provided. Moreover, the disclosure also contemplates examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

The present disclosure also relates to a computing system adapted, configured, or operated for performing the operations herein. This system may be specially constructed for the required purposes, or it may comprise a general purpose computer selectively activated or reconfigured by a computer program (e.g., instructions, code, etc.) stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved and other advantageous results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The examples described herein may be implemented in a variety of embodiments. For example, one embodiment includes a computing device including processing hardware (e.g., a processor or other processing circuitry) and memory hardware (e.g., a storage device or volatile memory) including instructions embodied thereon, such that the instructions, which when executed by the processing hardware, cause the computing device to implement, perform, or coordinate the electronic operations for these techniques and system configurations. Another embodiment discussed herein includes a computer program product, such as may be embodied by a machine-readable medium or other storage device, which provides the transitory or non-transitory instructions to implement, perform, or coordinate the electronic operations for these techniques and system configurations. Another embodiment discussed herein includes a method operable on processing hardware of the computing device, to implement, perform, or coordinate the electronic operations for these techniques and system configurations.

In further embodiments, the logic, commands, or transitory or non-transitory instructions that implement aspects of the electronic operations described above, may be provided in a distributed or centralized computing system, including any number of form factors for the computing system such as desktop or notebook personal computers, mobile devices such as tablets, netbooks, and smartphones, client terminals and server-hosted machine instances, and the like. Another embodiment discussed herein includes the incorporation of the techniques discussed herein into other forms, including into other forms of programmed logic, hardware configurations, or specialized components or modules, including an apparatus with respective means to perform the functions of such techniques. The respective algorithms used to implement the functions of such techniques may include a sequence of some or all of the electronic operations described above, or other aspects depicted in the accompanying drawings and detailed description below.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and example parameters, functions, and implementations described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled.

What is claimed is:

1. A method for generating a radiotherapy treatment plan, the method comprising:
    receiving, by processor circuitry, an input parameter related to a patient, the input parameter comprising at least one of dose information, one or more medical images, or one or more object segmentations;
    processing, by the processor circuitry, the input parameter with a machine learning technique to estimate a realizable plan parameter of a radiotherapy treatment plan, wherein the machine learning technique is trained to establish a relationship between the at least one of the dose information, the one or more medical images, or the one or more object segmentations of input parameter and a set of realizable radiotherapy treatment plan parameters to achieve a target radiotherapy dose distribution; and
    generating, by the processor circuitry, the radiotherapy treatment plan based on the estimated realizable plan parameter.

2. The method of claim 1, wherein processing the input parameter comprises:
    predicting, using the trained machine learning technique, an estimated treatment plan parameter of the radiotherapy treatment plan based on the input parameter; and
    generating the realizable plan parameter that corresponds to the estimated plan parameter.

3. The method of claim 2, wherein the realizable plan parameter is generated by solving an optimization problem.

4. The method of claim 3, wherein the optimization problem uses a loss function based on the set of realizable radiotherapy treatment plan parameters and the estimated plan parameter.

5. The method of claim 3, wherein the optimization problem is solved using at least one of a closed form solution, a gradient based scheme, or a stochastic optimization scheme.

6. The method of claim 2, wherein generating the realizable plan parameter comprises using at least one of an explicit differentiation process, composition of a fixed number of differentiable iterations, or a differentiable machine learning technique trained to estimate the realizable plan parameter.

7. The method of claim 2, wherein the estimated treatment plan parameter is incompatible with a radiotherapy device used to treat the patient.

8. The method of claim 7, wherein the estimated treatment plan parameter corresponds to a first dose distribution that is incompatible with the radiotherapy device; and
    wherein the realizable plan parameter is generated by identifying a subset of the set of the realizable radiotherapy treatment plan parameters that are compatible with the radiotherapy device and result in a second dose distribution that is within a specified threshold.

9. The method of claim 1, wherein the input parameter is further processed to achieve at least one of selected points from a dose-volume histogram or one or more radiobiological properties.

10. The method of claim 1, wherein the set of realizable radiotherapy treatment plan parameters includes at least one of machine parameters or a dose distribution.

11. The method of claim 1, wherein the machine learning technique is trained by optimizing a loss function based on a given radiotherapy treatment dose distribution and a given set of realizable radiotherapy treatment plan parameters.

12. The method of claim 11, where the optimization comprises at least one of a closed form solution, a gradient based scheme, or a stochastic optimization scheme.

13. The method of claim 1 further comprising training the machine learning technique by optimizing two loss functions using bilevel optimization.

14. The method of claim 13, further comprising:
    optimizing a first of the two loss functions based on a deviation between the at least one of the dose information, the one or more medical images, or the one or more object segmentations of input parameter and a set of estimated radiotherapy treatment plan parameters; and
    optimizing a second of the two loss functions based on a deviation between a result of optimizing the first loss function and realizable radiotherapy treatment plan parameters corresponding to the set of estimated radiotherapy treatment plan parameters.

15. A non-transitory computer readable medium comprising non-transitory computer readable instructions for generating a radiotherapy treatment plan, the computer readable instructions comprising instructions for performing operations comprising:
- receiving an input parameter related to a patient, the input parameter comprising at least one of dose information, one or more medical images, or one or more object segmentations;
- processing the input parameter with a machine learning technique to estimate a realizable plan parameter of a radiotherapy treatment plan, wherein the machine learning technique is trained to establish a relationship between the at least one of the dose information, the one or more medical images, or the one or more object segmentations of input parameter and a set of realizable radiotherapy treatment plan parameters to achieve a target radiotherapy dose distribution; and
- generating the radiotherapy treatment plan based on the estimated realizable plan parameter.

16. The non-transitory computer readable medium of claim 15, wherein the operations further comprise:
- predicting, using the trained machine learning technique, an estimated treatment plan parameter of the radiotherapy treatment plan based on the input parameter; and
- generating the realizable plan parameter that corresponds to the estimated plan parameter.

17. The non-transitory computer readable medium of claim 15, wherein the target radiotherapy dose distribution comprises at least one of a dose distribution, selected points from a dose-volume histogram, or one or more radiobiological properties.

18. A system for generating a radiotherapy treatment plan, the system comprising:
- a memory for storing instructions; and
- one or more processors for executing the instructions stored in the memory for performing operations comprising:
- receiving an input parameter related to a patient, the input parameter comprising at least one of dose information, one or more medical images, or one or more object segmentations;
- processing the input parameter with a machine learning technique to estimate a realizable plan parameter of a radiotherapy treatment plan, wherein the machine learning technique is trained to establish a relationship between the at least one of the dose information, the one or more medical images, or the one or more object segmentations of input parameter and a set of realizable radiotherapy treatment plan parameters to achieve a target radiotherapy dose distribution; and
- generating the radiotherapy treatment plan based on the estimated realizable plan parameter.

19. The system of claim 18, wherein the operations further comprise:
- predicting, using the trained machine learning technique, an estimated treatment plan parameter of the radiotherapy treatment plan based on the input parameter; and
- generating the realizable plan parameter that corresponds to the estimated plan parameter.

* * * * *